United States Patent [19]

Menache-Aronson et al.

[11] 4,447,416

[45] May 8, 1984

[54] PLASMA PROTEIN CONCENTRATES OF REDUCED THROMBOGENICITY AND THEIR USE IN CLINICAL REPLACEMENT THERAPY

[75] Inventors: Doris Menache-Aronson, Bethesda; David P. Kosow, Derwood; Carolyn L. Orthner, Rockville, all of Md.; H. Evan Behre, Alexandria, Va.

[73] Assignee: American National Red Cross, Washington, D.C.

[21] Appl. No.: 372,525

[22] Filed: Apr. 28, 1982

[51] Int. Cl.³ .......................................... A61K 35/16
[52] U.S. Cl. .................................................... 424/101
[58] Field of Search ....................................... 424/101

[56] References Cited

PUBLICATIONS

Curling, ed.–Methods of Plasma Protein Fractionation (Academic Press) 1980 pp. 60–61.
Suomela et al.–Chem. Abst. vol. 87 (1977) p. 51425w.
Liautaud et al.–Chem. Abst. vol. 94, (1981) p. 109,335e.
Suomela–Chem. Abst. vol. 86, (1977) p. 40,873u.
Yoshiok–Chem. Abst. vol. 89 (1978), pp. 213,384c.
Johnson et al.–Chem. Abst. vol. 95 (1981) p. 49245j.
Tanabe–Chem. Abst. vol. 93 (1980), p. 53851d.
VuKovich et al.–Chem. Abst. vol. 93 (1980), p. 40,663v.
Monahan et al.–Chem. Abst. vol. 94 (1981), p. 2528t.
Aronson, et al., "Toxicity of Factor IX Concentrates in Mice", *Develop. Biol. Standard.*, 44, 185–188 (1979).
Menache, "Prothrombin Complex Concentrates: Clinical Use", *Anal. N.Y. Acad. Sci.*, 370, 747–756 (1981).
Coan, et al., "Properties of Commercial Factor IX Concentrates", *Anal. N.Y. Acad. Sci.*, 370, 731–746 (1981).

*Primary Examiner*—Sam Rosen
*Attorney, Agent, or Firm*—Holman & Stern

[57] ABSTRACT

Plasma concentrates of vitamin-K dependent clotting factors of reduced thrombogenic potential useful for clinical replacement therapy in deficiency diseases of these clotting factors are provided. Preferably, concentrates substantially devoid of zymogens extraneous to the deficient factor are employed.

12 Claims, 3 Drawing Figures

PLASMA PROTEIN CONCENTRATES OF REDUCED THROMBOGENICITY AND THEIR USE IN CLINICAL REPLACEMENT THERAPY

The invention described herein was made in the course of work under a grant or award from the Department of Health and Human Services.

BACKGROUND OF THE INVENTION

Plasma contains a variety of proteins which have specific biologic functions, some known and well defined for a given protein, some still to be determined. Any plasma protein deficiency occurring either as a congenital disease or as an acquired state associated with a pathologic condition may indicate the need for replacement therapy. Because of technologic advances in the collection, storage and fractionation of plasma, a single unit of blood can now supply many concentrated, purified proteins for different therapeutic uses. For example, plasma was formerly the mainstay of hemophilia A and hemophilia B therapy; it is now used only when no other source of Factor VIII or Factor IX (the respective deficient factors) is available. It is currently considered poor practice to use unfractionated materials except in an emergency, because of the difficulty of achieving adequate and sustained therapeutic levels of the deficient materials without inducing circulatory overload. With the introduction of new techniques for protein purification and the recognition of congenital or acquired pathological states associated with specific protein deficiency, a number of plasma derivatives or concentrated fractions have been made available for the treatment of specific plasma protein deficiencies.

Prothrombin complex concentrates are clinically employed in current replacement therapy for patients with deficiencies of the vitamin K-dependent clotting Factors II, VII, IX and X. These concentrates, also referred to as Factor IX concentrates, Factor IX complex concentrates, and PPSB (prothrombin, proconvertin, Stuart factor, and antihemophilic B factor), have demonstrated efficacy in the treatment of hemophilia B (Christmas disease) by alleviating hemorrhagic episodes and preventing post-surgical complications. The efficacy of these Factor IX concentrates for replacement therapy in deficiencies of prothrombin (Factor II), Factor VII, and Factor X is also generally accepted, although the incidence of congenital deficiency of these factors is much rarer, and fewer data are available. Factor IX complex concentrates have, however, been implicated as a cause of thromboembolic complications and disseminated intravascular coagulation (DIC), particularly in patients with acquired deficiencies of the vitamin K-dependent clotting factors, especially those with liver disease. In patients with hemophilia B, thrombohemorrhagic complications occasionally result from infusions of conventional Factor IX complex concentrates. The reaction to these concentrates may be quite severe, with manifestations including superficial vein thrombosis, deep vein thrombosis, pulmonary embolism, and myocardial infarction. Fatalities believed to be directly attributable to commercial Factor IX complex concentrates have been documented.

While attempts have been made to devise reliable in vitro methods for the prediction of potential thrombogenicity in Factor IX complex concentrates and to identify the agent or agents present in these concentrates responsible for inducing thromboembolic complications, the results have been inconclusive. Experiments with animal models have demonstrated a correlation between non-activated partial thromboplastin time (NAPTT) and in vivo assays for thrombogenicity; the thrombingeneration test (TGt50) also correlates with in vivo test results. Using these and other in vitro tests, in conjunction with in vivo assays in animal models, researchers have suggested various causes of the thrombogenic activity associated with Factor IX complex concentrates prepared by standard methods, including Factors Xa, IXa, VIIa, and factors of the contact phase; Factor XIIa activation of prekallikrein; and high levels of zymogens extraneous to the deficient factor in the concentrates. Also considered as a possible factor in the adverse activity of the concentrates is Factor VIII bypassing activity. Unfortunately, available in vitro tests, including NAPPT and TGt50 are not reliably predictive of clinical thrombogenicity, and in vivo animal studies have proved inconclusive for various reasons. The lack of reliable in vitro tests and the impracticality of extensive in vivo testing has seriously hampered research attempts to isolate the causative agent or agents of the documented thromboembolic complications. As succinctly stated by Coan, et at. in "Properties of Commercial Factor IX Concentrates" (Ann. N.Y. Acad. Sci., 731-746; 734, 789, 1981), "Various investigators have proposed at one time or another than any of the activated coagulation factors are the cause of thrombogenicity. These include Factors VIIa, IXa, Xa, and XIa. There are no consistent results. The actual thrombogenic agent may be none, one, several or all of the above . . . . Results [of extended investigations] suggest that some as yet unidentified component of the Factor IX preparation may well be involved in the occurrence of thrombogenic reactions independent of the state or concentration of the major vitamin K-dependent factors."

It is accordingly highly desirable to provide concentrated plasma protein fractions useful for replacement therapy in congenital or acquired deficiencies of vitamin K-dependent clotting factors but which have little or no thrombogenic potential. From a practical standpoint, it is particularly desirable to provide a Factor IX concentrate devoid of thrombogenic agents but retaining clinical activity for the control of hemorrhage in hemophilia B patients, owing to the relatively more common incidence of this deficiency disease.

SUMMARY OF THE INVENTION

The invention is predicated on the identification of products useful in replacement therapy for congenital and acquired deficiencies of vitamin F-dependent clotting factors having little or no thrombogenic potential, as assessed by animal models based on the Wessler venous stasis technique (Wessler, et al., "Biologic Assay of a Thrombosis-inducing Activity in Human Serum", J. Appl. Physiol., 14:943-946 1959) and a modification of the method of Prowse and Williams (Prowse, et at., "A Comparison of the In Vitro and In Vivo Thrombogenic Activity of Factor IX Concentrates Using Stasis and Non-stasis Rabbit Models", Thromb. Haemostas., 44:82-86, 1980). Pursuant to the postulation that vitamin K-dependent clotting factors in conventional Factor IX complex concentrates which are extraneous to the deficient factor are responsible for thromboembolic complications in recipients of replacement therapy by overloading the coagulation mechanism, non-thrombogenic plasma protein fractions for replacement therapy have been developed which are substantially devoid of extraneous vitamin K-dependent clotting factors. In particular, it has been discovered that conventional Factor IX complex concentrate purified with respect to Factors II, VII, and X has little or no potential for causing thromboembolic complications in hemophilia B recipients based on animal safety data; similarly, Factor X concentrate purified with respect to Factors II, VII and IX exhibits little or no thrombogenic potential, again based on animal safety data. The invention accordingly provides a method for the treatment of vitamin K-dependent clotting factor deficiencies comprising a replacement therapy based on the administration of a plasma protein fraction concentrated with respect to the deficient clotting factor and substantially devoid of extraneous clotting factors. In particular, the invention provides a method for the treatment of hemophilia B comprising a replacement therapy based on the administration of a Factor IX plasma concentrate substantially devoid of Factors II, VII, and X, and a method for the treatment of a Factor X deficiency comprising a replacement therapy based on the administration of a Factor X plasma concentrate substantially devoid of Factors II, VII, and IX. The invention further provides an improved plasma concentrate of a vitamin K-dependent clotting factor suitable for clinical use in replacement therapy, and a method of preparing the improved concentrate.

DETAILED DESCRIPTION OF THE INVENTION

Figure 1:
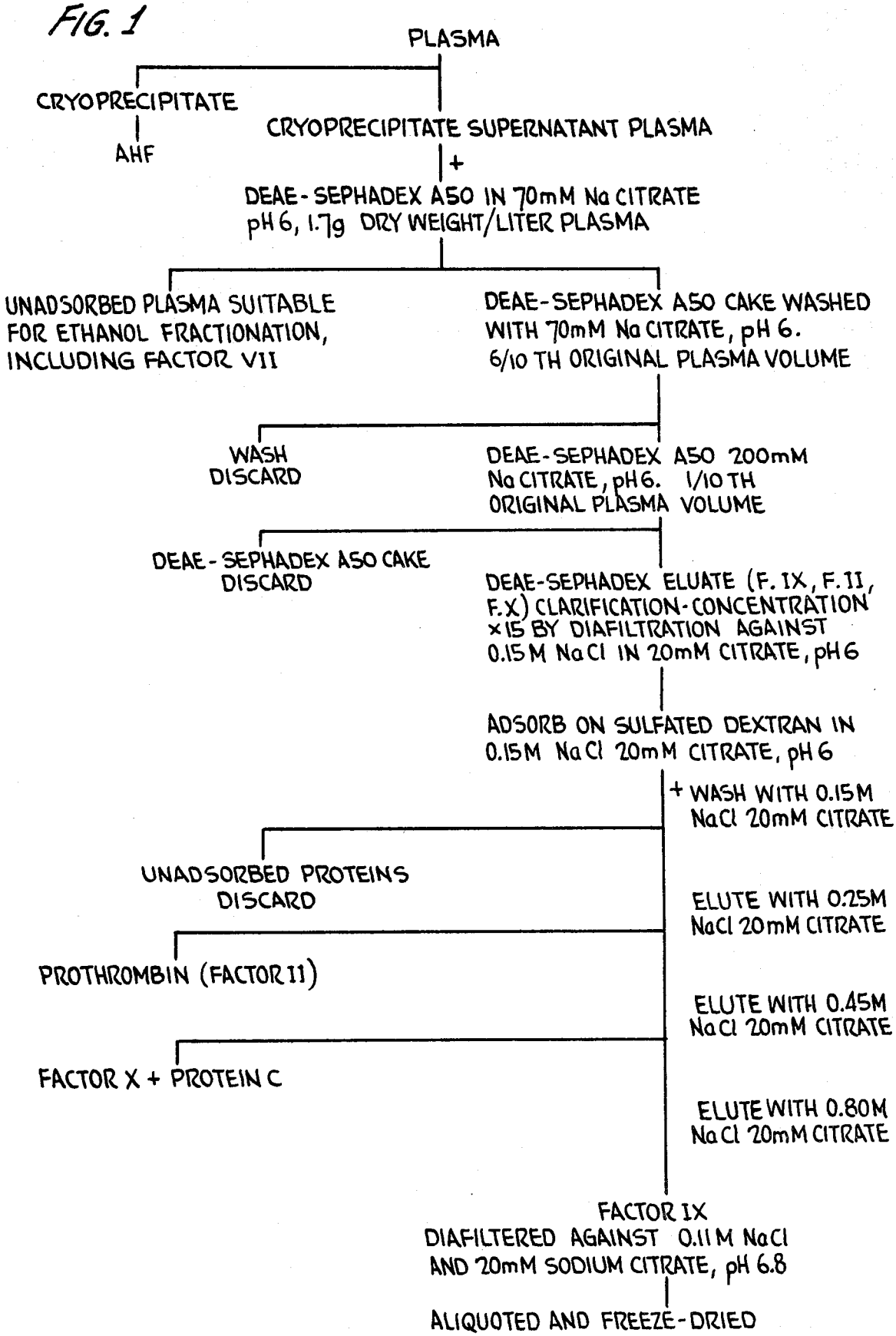
FIG. 1 is a flow diagram exemplifying the preparation of Factor IX and Factor X concentrates according to the invention.

According to the invention, a Factor IX concentrate substantially devoid of Factors II, VII and X is employed in replacement therapy for the treatment of hemophilia B in humans. Suitable starting materials for the preparation of this concentrate are whole plasma, plasma cryosupernatant, or Cohn Effluent I. Such starting materials are then purified to substantially remove clotting Factors II, VII and X, for example by anion-exchange chromatography on DEAE-Sephadex or DEAE-cellulose followed by adsorption on a water-insoluble cross-linked sulfated polysaccharide gel matrix of the type described in U.S. Pat. No. 3,842,061 to Andersson, et at. Commercial Factor IX complex concentrates can also be employed as starting material, in which case the initial step of anion-exchange chromatography can usually be eliminated. A particularly useful procedure for the purification of Factor IX is described by Miletich, et at., in "The Synthesis of Sulfated Dextran Beads for Isolation of Human Coagulation Factors II, IX and X" (Anal. Biochem., 105:304–310, 1980). In the improved process of the invention for the preparation of concentrates suitable for clinical use, the Miletich procedure is modified by elimination of the initial step of barium precipitation, and omission of treatment with diisopropylfluorophosphate and benzamidine, to avoid the possibility that these toxic materials might be present in the infusion in harmful quantities. Preferably, adsorption of the starting Factor IX complex concentrate is followed by stepwise elution or gradient elution with increasing concentrations of NaCl to permit recovery of the Factor II, X and Protein C by-products. Factor X concentrates according to the invention for use in replacement therapy for deficiencies of this factor conveniently comprise the Factor X fraction eluted according to the purification scheme of the invention, exemplified in the flow diagram illustrated in FIG. 1. Since Protein C functions as an anticoagulant, it is surprising that the Factor IX concentrate purified with respect to this protein is non-thrombogenic.

The resultant purified concentrates are substantially devoid of extraneous clotting factors and exhibit substantially no thrombogenic potential as measured by the Wessler venous stasis technique in rabbits, at the therapeutic dosage levels. Preferred Factor IX concentrates for clinical use contain extraneous clotting Factors II, VII and X in amounts of less than about 1%, 0.5%, and 5% by specific activity (u/mg) of Factor IX, respectively, and, most preferably, are substantially devoid of these extraneous clotting factors. Preferred Factor X concentrates for clinical use contain Factors II, VII, and IX in amounts of less than about 1%, 0.5%, and 15% by specific activity of Factor X, respectively, and, most preferably, are substantially devoid of these extraneous clotting factors.

The reduced risk of thrombotic episodes attendant upon the clinical use of the purified Factor IX and X concentrates according to the present invention also permits infusions of these factors at higher dosage levels for more effective therapy. While dosage levels comparable to those recommended by standard clinical protocols for Factor IX complex concentrates are highly effective, if desired, dosages in excess of these levels, for example, up to twice the standard dosage, may be used, based upon the toxicity data obtained from animal trials. Generally, dosages sufficient to bring the deficient factors to a circulating level of from about 30% to about 50% of normal are recommended, usually requiring from about 30 to 50 units/kg body weight.

EXAMPLES

A. Purification of Factor IX Complex Concentrates

Example 1

Several batches of Factor IX concentrate were prepared according to the flow diagram illustrated in FIG. 1. For each liter of human cryosupernatant plasma, 1.7 g of DEAE-Sephadex A-50 (previously swollen in 0.07 M Na-Citrate, pH 6.0) was added. The mixture was stirred gently for 1 hr, the supernatant decanted and the resin collected in a polyethylene Buchner funnel (70μ porosity) and washed with 0.07 M Na-Citrate, pH 6.0 until the $A_{280}$ reached a plateau value of about 0.2 and the color of the resin changed from deep green to light blue (approximately 0.64 l/l original plasma). The Factor IX-containing fraction was then eluted with 0.2 M Na-Citrate, pH 6.0 (approximately 0.08 l/l original plasma). The DEAE-Sephadex eluate was diafiltered into 0.15 M NaCl, 0.02 M Na-Citrate, pH 6.0, to a final volume of 15 ml/l original plasma and was then loaded onto a column of sulfated dextran (previously equilibrated with 0.15 M NaCl, 0.02 M Na-Citrate, pH 6.0) which was prepared by the method of Miletich, et al. For each liter of original plasma, 10 ml of sulfated dextran was required. After the breakthrough protein eluted from the column, the NaCl concentration was increased to 0.25 M to elute the prothrombin; Factor X was eluted with 0.45 M NaCl and Factor IX was eluted with 0.8 M NaCl. All the eluting solutions contained 0.02 M Na-Citrate, pH 6.0. The stepwise elution of the clotting factors from the sulfated-dextran column yields prothrombin, a Factor X concentrate contaminated with both Protein C and a small but significant amount of Factor IX and a Factor IX concentrate essentially free of Factor X and prothrombin. A summary of a purification is shown in Table 1. The overall yield of Factor IX is 18% with an 880-fold increase in specific activity. Based on the specific activity of pure human Factor IX of 325 or 275, the resultant Factor IX concentrate is between 5 and 6% pure in terms of protein. On an activity basis, this preparation of Factor IX contains less than 1% of either prothrombin or Factor X contamination. Factor X contamination of Factor IX concentrate is typically below 4% while prothrombin contamination is typically below 1%.

B. Evaluation of Thrombogenicity of Purified Factor IX Concentrate

Example 2

Stasis Rabbit Model.

A model using the venous stasis technique of Wessler, et al., supra, was employed for testing several batches of purified Factor IX concentrate obtained according to Example 1. The jugular vein of a rabbit was ligated 10–15 seconds after injecting the sample to be tested in the marginal vein of the ear. The formation of thrombi in the isolated vein segment was determined by visual inspection after 10 minutes and scored from 0 to 4, a score of 4 indicating complete occlusion of the vessel. The results obtained on several batches of Factor IX concentrate from Example 1 are given in Table 2. Preparations were found to be non-thrombogenic with dosages of Factor IX concentrate ranging from 150 to as high as 380 units/kg of rabbit body weight. In contrast, a commercial Factor IX complex concentrate,

TABLE 1

| FACTOR IX CONCENTRATE - CHARACTERISTICS | | | | | |
|---|---|---|---|---|---|
| | Units ×10⁻³ | Protein GM | Specific Activity u/mg** | Yield % | Ratio II:X:IX |
| Plasma | 125* | 6875 | 0.02 | — | 1:1:1 |
| DEAE-Eluate | 43* | 20 | 2.15 | 34 | 1:0.5:0.9 |
| Sulfated-Dextran Fractions: | | | | | |
| Prothrombin | 22.3 | 5.1 | 4.4 | 18 | 1:0.02:0 |
| Factor X | 31.4 | 0.79 | 39.7 | 25 | 0.002:1:0.6 |
| Factor IX | 22.9 | 1.3 | 17.6 | 18 | 0.002:0.004:1 |

*Factor IX Units
**A unit (u) is defined as the biological activity of a protein/ml of normal plasma.

TABLE 2

| STASIS RABBIT MODEL | | | | | |
|---|---|---|---|---|---|
| | Lot | Dose (u/kg)** | | | |
| Preparation | # | IX | X | II | Score |
| Commercial Factor IX Complex (containing Factors II, VII, IX, X) | — | 56.6 100.0 | 53.9 117.0 | 51.1 86.4 | 1 2 |
| DEAE-Sephadex A-50 Eluate | 16* | 103.0 | 60.6 | 113.0 | 2 |
| Factor IX | 15* | 150.0 | 4.5 | 0.9 | 0 |
| | 15 | 201.0 | 6.0 | 1.2 | 0 |
| | 16 | 201.0 | 0.5 | 0.3 | 0 |
| | 16 | 380.0 | 0.97 | 0.6 | 0 |

TABLE 2-continued

| STASIS RABBIT MODEL | | | | | |
|---|---|---|---|---|---|
| | Lot | Dose (u/kg)** | | | |
| Preparation | # | IX | X | II | Score |
| Prothrombin | 16 | — | — | 100.0 | 1 |
| | 16 | — | — | 200.0 | 3 |
| Factor X | 16 | 12.2 | 139.0 | 0.3 | 1 |

*Laboratory prepared lots.
**A unit (u) is defined as the biological activity of a protein/ml of normal plasma.

as well as the DEAE-Sephadex eluate (obtained during the first step of the fractionation procedure of Example 1), both of which contain significant amounts of prothrombin and Factor X, induced clots with scores ranging from 1 to 2 when injecting dosages of Factor IX ranging from 56 to 100 units/kg.

Example 3

Non-Stasis Rabbit Model.

Comparable results were obtained when testing the DEAE-Sephadex eluate and the Factor IX concentrate of Example 1 using a rabbit non-stasis model. In this procedure, 3.6 to 4 kg male white rabbits were sedated with NEMBUTAL (27 mg/kg). A polyethylene cannula was introduced into the carotid artery. Blood samples were obtained from this cannula 30 minutes prior to and immediately before (0 time) the test material was injected at a rate of 2 ml/min. Blood samples were then taken at various times up to 2 hours after test sample injection. The blood samples (7 ml) were collected into plastic tubes containing 0.15 ml 1 M citrate. Three ml of the citrated blood was then placed into a second tube containing 6 mg of soybean trypsin inhibitor. The citrated sample was used for the coagulation factor assays and platelet count, while the soybean trypsin inhibitor-treated blood was used to measure fibrinogen. As shown in Table 3, the eluate containing Factor IX, prothrombin, and Factor X, when infused at 100 u/kg Factor IX, induced coagulation changes compatible with DIC as evidenced by a decrease in the platelet count, and decreased concentrations of Factors V and VIII, whereas the Factor IX concentrate, when infused at 200 u/kg, did not change the coagulation parameters apart from a slight decrease in the platelet count and a predictable rise in the Factor IX level (Table 4). Preliminary results

TABLE 3

| DEAE-SEPHADEX A-50 ELUATE* NON-STASIS RABBIT MODEL | | | | | | | |
|---|---|---|---|---|---|---|---|
| | Percent of Preinjection Value** | | | | | | |
| | Time (min) | | | | | | |
| | −30 | 0 | 15 | 30 | 60 | 90 | 120 |
| Factor IX | 100 | 98 | 168 | 165 | 153 | 121 | 107 |
| Factor X | 100 | 110 | 460 | 426 | 347 | 282 | 287 |
| Prothrombin | 100 | 98 | 620 | 606 | 478 | 450 | 398 |
| Factor VIII | 100 | 94 | 92 | 93 | 59 | 39 | 26 |
| Factor V | 100 | 105 | 103 | 94 | 64 | 39 | 28 |
| Fibrinogen | 100 | 102 | 93 | 83 | 57 | 44 | 32 |
| Platelets | 100 | 98 | 75 | 66 | 46 | 37 | 32 |

*Dosage = 100 u/kg Factor IX
**Average of three (3) rabbits

TABLE 4

FACTOR IX CONCENTRATE*
NON-STASIS RABBIT MODEL

| | Percent of Preinjection Value Time (min) | | | | | |
|---|---|---|---|---|---|---|
| | −30 | 0 | 30 | 60 | 90 | 120 |
| Factor IX | 100 | 89 | 517 | 288 | 360 | 306 |
| Factor X | 100 | 100 | 100 | 93 | 96 | 92 |
| Prothrombin | 100 | 98 | 92 | 89 | 91 | 84 |
| Factor VIII | 100 | 101 | 121 | 103 | 110 | 100 |
| Factor V | 100 | 100 | 96 | 96 | 88 | 88 |
| Fibrinogen | 100 | 101 | 111 | 83 | 80 | 87 |
| Platelets | 100 | 86 | 73 | 70 | 67 | 68 |

*Dosage = 200 u/kg Factor IX
**Average of three (3) rabbits omer, and degradation products, were obtained for 24–48 hours after infusion. Postmortem examination was performed at the time of death or 14 days after infusion. Five (5) different sources of nonactivated and 2 sources of activated Factor IX complex concentrates (PCC) were infused. Seven of 8 pigs receiving >50 units/kgm as a single infusion of nonactivated PCC had 1+ to 4+ fibrin monomers at 15 minutes, whereas 7 of 8 receiving activated PCC had similar changes at doses >25 units/kgm. Evidence of severe IVC occurred in all 5 animals receiving 100 units/kgm of either material. Overt IVC was associated with decreased platelet count, fibrinogen, presence of fibrin monomers, and postmortem thrombosis. Subclinical IVC was associated with increased monomers with

TABLE 5

Pig No. 13 treated with ARC - PTC concentrate No. 81-91 at 50 u Factor IX/kg body weight

| | Pre 1 | Pre 2 | 15+ | 1 hr | 2 hr | 3 hr | 4 hr | 5 hr | 6 hr |
|---|---|---|---|---|---|---|---|---|---|
| Platelet Count* | 245 | 265 | 235 | 270 | 140 | 185 | 147 | 140 | 150 |
| Capillary | 8 | 2.6 | 2.5 | 1.8 | 2.1 | 2.1 | 2.1 | 2.0 | 2.0 |
| Fibrinogen** | 1.8 | 2.6 | 2.6 | 1.8 | 2.1 | 2.1 | 2.1 | 2.0 | 2.0 |
| Protamine Test For Fibrin Monomer | neg. | neg. | ± | ± | ± | ± | ± | ± | 2 |
| Prothrombin Time+ | 14.7 | 15.3 | 13.5 | 16.5 | 17.0 | 17.0 | 16.9 | 16.9 | 8.8 |
| | 15.9 | 16.0 | 14.3 | 16.8 | 17.8 | 17.8 | 17.3 | 17.3 | 9.8 |
| Partial Thrombo-Plastin time+ | 45.9 | 65.8 | 29.5 | 20.5 | 26.3 | 25.8 | 23.4 | 24.0 | 30.9 |
| | 47.3 | 66.0 | 30.8 | 22.3 | 26.4 | 26.5 | 24.3 | 25.3 | 31.3 |
| White Count* | 30.5 | 22.6 | 36.0 | 32.3 | 21.3 | 29.0 | 26.2 | 27.2 | 27.2 |
| Fibrinogen++ | 268 | 374 | −35 | 441 | 222 | 353 | 342 | 276 | 308 |

| | 8 hr | 11 hr | 24 hr | 27½ hr | 30 hr | 48 hr | 53 hr | 74 hr | 95 hr |
|---|---|---|---|---|---|---|---|---|---|
| Platelet Count* | 150 | 165 | 145 | 160 | 120 | 165 | 130 | 204 | 150 |
| Capillary | 2.2 | 2.2 | 2.1 | 2.2 | 2.0 | 1.8 | 2.0 | 2.0 | 2.2 |
| Fibrinogen** | 2.2 | 2.3 | 2.1 | 2.2 | 2.2 | 2.0 | 2.0 | 2.2 | 2.2 |
| Protamine Test For Fibrin Monomer | 2 | 2 | 1 | 1 | 1 | + | neg. | neg. | neg. |
| Prothrombin Time+ | 14.5 | 15.4 | 14.8 | 13.3 | 13.5 | 15.3 | 16.8 | 14.9 | 16.8 |
| | 14.8 | 15.8 | 16.0 | 13.4 | 13.9 | 16.0 | 17.5 | 15.5 | 17.5 |
| Partial thrombo-Plastin time+ | 35.5 | 52.8 | 41.5 | 35.3 | 34.5 | 65.0 | 104.9 | 54.5 | 53.8 |
| | 36.8 | 64.5 | 44.8 | 37.5 | 35.3 | 69.8 | 113.4 | 58.8 | 68.9 |
| White Count* | 23.5 | 28.9 | 24.2 | 20.3 | 16.2 | 19.4 | 18.5 | 23.5 | 19.1 |
| Fibrinogen++ | 365 | 419 | 367 | 388 | 399 | 297 | 357 | 383 | 440 |

Gross autopsy results 8/31/81 revealed no scarring or regeneration related to the PTC injection, however microscopic results indicated some evidence of thrombotic activity
*X10³/mm³
**Heat-precipitable fibrinogen, mm
+Seconds (duplicate samples)
++Clottable fibrinogen, mg/dl with three (3) rabbits showed that when prothrombin is tested in this model, minimal changes occur except for a decrease in platelet count and Factor VIII level. A modification of the non-statis model of Prowse, et al. (supra) and Triantaphyllopolous, "Intravascular Coagulation Following Injection of Prothrombin Complex", Am. J. Clin. Path., 57:603–610, 1972, was employed.

Example 4

Porcine Model.

Harrison, et al., (Clinical Research, 30:318a, 1982) reported that a more sensitive animal in which to assess the thrombogenicity of Factor IX concentrate is the mini-pig (small pig). The Harrison porcine model is a model developed for the evaluation of thrombogenicity of prothrombin complex concentrate. Internal jugular/superior vena cava I.V. silastic tubing was placed in 18 pigs aged 4 mos. (20–25 kgms) under general anesthesia. Catheter placement was observed for 24 hours before infusion. Sequentially obtained blood samples to monitor intravascular coagulation (IVC) including platelet count, PT, PTT, TT, procoagulant factors, fibrin monomer, and degradation products, were obtained for variable changes in platelet count and fibrinogen, but postmortem evidence of renal injury. Control infusions (2 pigs) of albumin were negative.

Preliminary experiments were performed by these investigators with the DEAE-Sephadex eluate obtained according to Example 1, which contains Factors II, IX and X, and minor amounts of Factor VII (prior to adsorption and elution from sulfated dextran). This eluate was injected at a dose of 50 units of Factor IX/kg body weight and resulted in evidence of thrombotic activity (Table 5).

When one lot of purified Factor IX concentrate according to Example 1 was injected at a dose of 50 units/kg the gross autopsy revealed no scarring or regeneration related to the product and the microscopic results showed no abnormalities. The autopsy details are summarized in Table 6.

A purified Factor IX concentrate obtained according to Example 1 was injected at a level of 200 units/kg body weight. Autopsy results showed that all tissues were normal on gross examination, with no apparent residual scarring as a result of the infusion. Autopsy results are summarized in Table 7.

C. Preparation of Purified Factor IX Concentrate For Clinical Use

Example 5

The purified Factor IX concentrate obtained according to Example 1 was freeze-dried and stored at 1° to 10° C. The powdered concentrate was apportioned into dosages for clinical use. The dosages were reconstituted with 10 ml. of water prior to injection to provide an infusion isotonic with blood and of the following composition:

| Ingredient |  |  | Ranges |  |
|---|---|---|---|---|
| Sodium Chloride | 0.11 | M |  |  |
| Sodium Citrate | 20 | mM |  |  |
| Total Protein | 28 | mg | 25-31 | mg |
| Factor II (prothrombin) | 2 | units | 1-4 | units |
| Factor X | 4 | units | 2-8 | units |
| Factor VII | <1 | unit |  |  |
| Factor IX | 500 | units | 450-550 | units |
|  | ph ~6.8 |  |  |  |

D. Evaluation Of Thrombogenicity Of Purified Factor X Concentrate

Example 6

The Factor X fraction obtained after elution from sulfated-dextran with 0.45 M NaCl in the Factor IX purification procedure of Example 1 was tested for thrombogenicity according to the stasis and non-stasis models of Examples 2 and 3.

Figure 2:
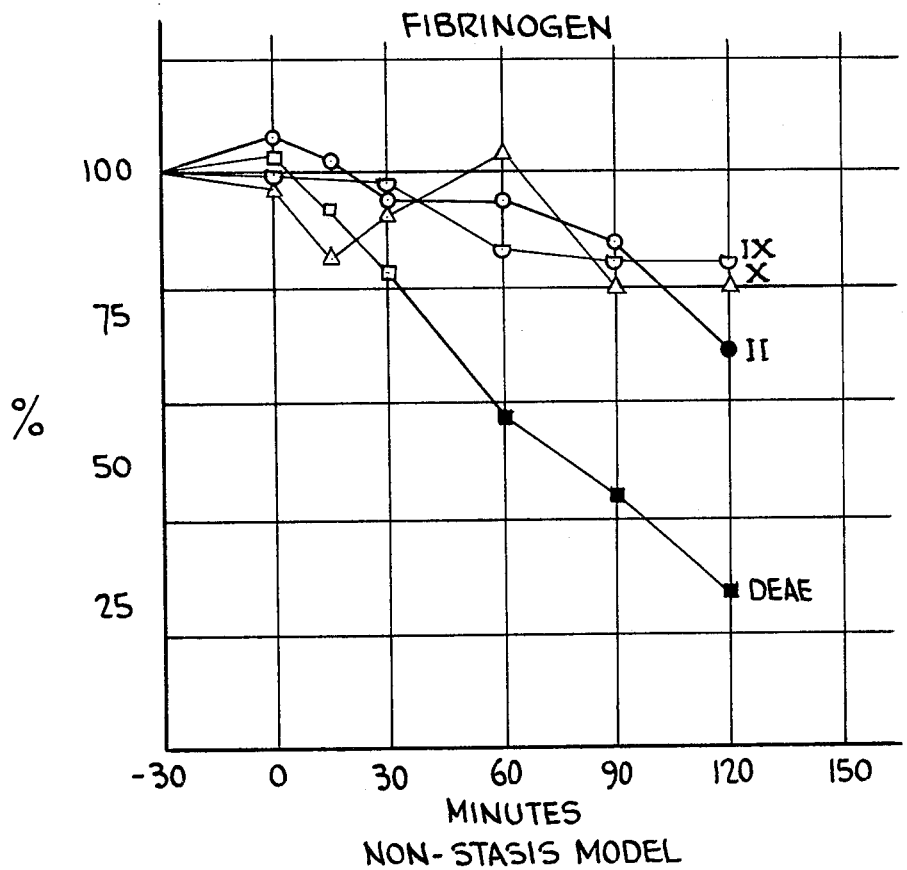
FIG. 2 is a graph of fibrinogen levels over time (non-stasis model) after administration of the concentrates of the invention.

As illustrated in FIG. 2, in the non-stasis model (3 rabbits each) the eluate fraction containing Factors II, IX and X (DEAE), when infused at 100μ of the fraction per kilogram of body weight, induced coagulation changes compatible with DIC as evidenced by a decrease in fibrinogen level. In contrast, the purified Factor X concentrate only slightly lowered the fibrinogen level in this model. (The solid points in the graph have statistical significance at $p<0.05$, based on the Two-Tailed Student's t-Test.)

Figure 3:
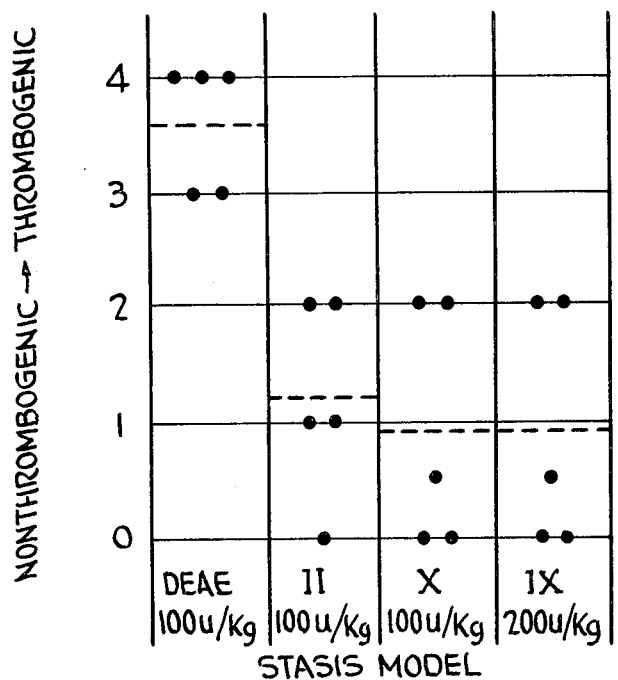
FIG. 3 is a graph of Wessler venous stasis scores after administration of the concentrates according to the invention.

As illustrated in FIG. 3, in the stasis model, average scores (indicated by dotted lines) did not exceed 1 for the Factors II, IX, and X concentrates obtained according to Example 1. In contrast, the average score for the fraction containing Factors II, X, and IX (DEAE) was greater than 3.5. The average scores of the Factor IX and Factor X concentrates were the same; however, the Factor IX concentrate was administered at twice the dosage (200 u/kg) as the Factor X concentrate 100 u/kg.

TABLE 6

Pig No. 14 treated with ARC Factor IX Concentrate Lot NO. 81-91 at a level of 50 u/kg Factor IX (body weight)

|  | Pre 1 | Pre 2 | 15+ | 1 hr | 2 hr | 3 hr | 4 hr | 5 hr | 6 hr |
|---|---|---|---|---|---|---|---|---|---|
| Platelet Count* | 390 | 380 | 425 | 360 | 390 | 340 | 325 | 280 | 295 |
| Capillary | 2.1 | 2.8 | 2.7 | 1.8 | 1.9 | 2.3 | 2.1 | 2.2 | 2.2 |
| Fibrinogen** | 2.2 | 2.8 | 2.8 | 11 | 2.0 | 2.3 | 2.2 | 2.2 | 2.2 |
|  |  |  |  | 1.8 |  |  |  |  |  |
| Protamine Test For Fibrin Monomer | neg. | neg. | neg. | neg. | neg. | neg. | neg. | neg. | neg. |
| Prothrombin Time+ | 13.9 | 14.0 | 15.5 | 18.0 | 17.5 | 19.0 | 18.0 | 18.9 | 14.5 |
|  | 14.3 | 14.8 | 15.8 | 18.8 | 19.8 | 20.3 | 19.3 | 20.3 | 14.8 |
| Partial thrombo-Plastin time+ | 31.0 | 30.0 | 57.8 | 26.0 | 26.3 | 25.0 | 26.3 | 32.8 | 29.5 |
|  | 32.3 | 30.8 | 59.0 | 31.3 | 28.0 | 26.3 | 27.5 | 33.4 | 31.3 |
| White Count* | 17.4 | 22.4 | 20.9 | 16.5 | 26.8 | 24.5 | 23.4 | 23.2 | 22.6 |
| Fibrinogen++ | 369 | 422 | 516 | 330 | 297 | 435 | 423 | 435 | 281 |
|  | 8 hr | 11 hr | 23 hr | 27 hr | 30 hr | 48 hr | 58 hr | 74 hr | 94 hr |
| Platelet Count* | 345 | 345 | 290 | 300 | 350 | 370 | 345 | 380 | 390 |
| Capillary | 2.3 | 2.0 | 2.2 | 2.0 | 2.2 | 2.1 | 2.2 | 2.2 | 2.0 |
| Fibrinogen** | 2.3 | 2.1 | 2.2 | 2.4 | 2.2 | 2.2 | 2.2 | 2.2 | 2.2 |
| Protamine Test For Fibrin Monomer | neg. | neg. | neg. | neg. | neg. | neg. | neg. | neg. | neg. |
| Prothrombin Time+ | 15.0 | 16.0 | 14.5 | 15.0 | 15.3 | 13.9 | 15.0 | 14.8 | 14.8 |
|  | 15.3 | 16.3 | 14.8 | 15.3 | 15.5 | 14.8 | 15.8 | 14.9 | 15.0 |
| Partial thrombo-Plastin time+ | 31.0 | 43.9 | 58.3 | 49.4 | 46.5 | 49.5 | 46.6 | 49.0 | 32.5 |
|  | 32.3 | 49.3 | 59.0 | 49.9 | 49.4 | 50.9 | 51.2 | 54.3 | 33.3 |
| White Count* | 23.7 | 19.5 | 19.2 | 23.1 | 27.0 | 19.1 | 23.7 | 21.5 | 19.0 |
| Fibrinogen++ | 393 | 415 | 367 | 370 | 339 | 408 | 374 | 435 | 472 |

Gross autopsy results 9/1/81 revealed no scarring or regeneration related to the Factor IX concentrate injected. Commercial concentrates of PTC yield significant changes at the above dosage level.
*X10³/mm³
**Heat-precipitable fibrinogen, mm
+Seconds, duplicate samples
++Clottable Fibrinogen, mg/dl

TABLE 7

Pig No. 17 treated with ARC Factor IX concentrate Lot 18-91 at a level of 200 IU/kg body weight

|  | Pre 1 | Pre 2 | Pre 3 | 15+ | 30+ | 1 hr | 2 hr |
|---|---|---|---|---|---|---|---|
| Platelet Count* | 595 | 430 | 380 | 360 | 320 | 370 | 275 |

TABLE 7-continued

Pig No. 17 treated with ARC Factor IX concentrate Lot 18-91 at a level of 200 IU/kg body weight

|  |  |  |  |  |  |  |  |
|---|---|---|---|---|---|---|---|
| Capillary | — | 1.5 | 1.7 | 1.6 | 1.4 | 1.4 | 1.2 |
| Fibrinogen** | — | 1.5 | 1.7 | 1.6 | 1.4 | 1.6 | 1.4 |
| Protamine Test For Fibrin Monomer | — | neg. | neg. | neg. | neg. | neg. | ± |
| Prothrombin | 16.5 | 15.0 | 13.3 | 18.4 | 16.9 | 17.3 | 16.0 |
| Time+ | 16.8 | — | 13.5 | 18.8 | 17.8 | 17.5 | 16.3 |
| Partial thrombo- | 16.0 | 24.5 | 19.3 | 15.5 | 15.0 | 15.0 | 11.8 |
| Plastin Time+ | 16.3 | 24.3 | 19.5 | 17.3 | 15.8 | 16.3 | 12.5 |
| White Count* | 14.0 | 13.4 | 11.5 | 7.3 | 3.5 | 5.6 | 4.5 |
| Fibrinogen++ | 300 | 300 | 340 | 320 | 280 | 300 | 260 |

|  | 3 hr | 4 hr | 5 hr | 6 hr | 7 hr | 8 hr | 11½ hr |
|---|---|---|---|---|---|---|---|
| Platelet Count* | 225 | 235 | 175 | 215 | 205 | 220 | 270 |
| Capillary | 1.2 | 1.4 | 1.5 | 1.4 | 1.4 | 1.4 | 1.4 |
| Fibrinogen** | 1.2 | 1.4 | 1.5 | 1.4 | 1.5 | 1.4 | 1.5 |
| Protamine Test For Fibrin Monomer | 4+ | 4+ | ± | ± | neg. | neg. | |
| Prothrombin | 18.0 | 16.5 | 14.9 | 13.1 | 14.4 | 14.0 | 13.4 |
| Time+ | 18.8 | 16.8 | 15.4 | 13.9 | 14.5 | 14.3 | 13.8 |
| Partial Thrombo- | 57.6 | 14.5 | 22.0 | 16.0 | 18.0 | 18.5 | 17.5 |
| Plastin Time+ | 62.5 | 15.3 | 22.3 | 16.3 | 18.8 | 19.4 | 18.8 |
| White Count* | 4.4 | 4.7 | 5.0 | 4.6 | 6.7 | 7.0 | 6.7 |
| Fibrinogen++ | 240 | 280 | 300 | 280 | 300 | 280 | 300 |

|  | 22½ hr | 24 hr | 26 hr | 28 hr | 49 hr | 52½ hr | 77 hr | 95 hr |
|---|---|---|---|---|---|---|---|---|
| Platelet Count* | 325 | 345 | 270 | 295 | 385 | 340 | 370 | 475 |
| Capillary | 1.4 | 1.4 | 1.4 | 1.4 | 1.4 | 1.2 | 1.3 | 1.4 |
| Fibrinogen** | 1.5 | 1.8 | 1.5 | 1.5 | 1.4 | 1.3 | 1.4 | 1.4 |
| Protamine Test For Fibrin Monomer | neg. | neg. | neg. | neg. | neg. | neg. | neg. | neg. |
| Prothrombin | 12.9 | 11.8 | 12.5 | 13.3 | 15.3 | 13.0 | 13.8 | 14.8 |
| Time+ | 13.0 | 12.4 | 12.8 | 13.5 | 16.5 | 13.8 | 14.0 | 15.5 |
| Partial thrombo- | 18.0 | 15.5 | 16.5 | 19.8 | 37.3 | 15.0 | 16.3 | 19.0 |
| Plastin Time+ | 18.3 | 16.3 | 16.8 | 20.0 | 28.9 | 15.8 | 16.5 | 19.3 |
| White Count | 9.3 | 10.6 | 8.3 | 10.3 | 13.2 | 12.9 | 13.7 | 14.2 |
| Fibrinogen++ | 300 | 360 | 300 | 300 | 280 | 260 | 280 | 280 |

Gross autopsy results on this animal showed that all tissues were normal. There was no apparent residual scarring as a result of the infusion. Microscopic studies have not been completed.
*× $10^3/mm^3$
**Heat-precipitable fibrinogen, mm
+Seconds, duplicate samples
++Clottable fibrinogen, ml/dl

What is claimed is:

1. An intermediate purified non-thrombogenic factor IX concentrate containing factor IX in therapeutic amounts up to a specific activity of about 17.6 (u/mg. protein), and containing factors II, VII, and X in non-thrombogenic amounts of less than about 1%, 0.5%, and 5% by specific activity of factor IX, respectively.

2. In a method for the treatment of a deficiency of factor IX in humans of the type wherein a partially-purified therapeutic plasma protein fraction concentrated with respect to factors II, IX, and X, or with respect to factors II, VII, IX and X to provide a factor IX concentrate is administered to correct the deficiency, the improvement comprising administering the non-thrombogenic concentrate of claim 1.

3. The non-thrombogenic concentrate of claim 1, produced by the process consisting of the steps of
(a) ion-exchange chromatography of a plasma cryosupernatant to provide a Factor IX fraction containing Factors II, IX and X; and
(b) adsorption of the Factor IX fraction on a water-insoluble cross-linked sulfated polysaccharide gel matrix adsorbing agent followed by elution of the Factor IX fraction components from the gel matrix with increasing concentrations of an eluting agent to sequentially provide a Factor II fraction, a Factor X fraction, and a Factor IX fraction.

4. The non-thrombogenic concentrate of claim 1, produced by the process consisting of adsorption of a Factor IX fraction containing Factors II, IX, and X on a water-insoluble cross-linked sulfated polysaccharide gel matrix adsorbing agent followed by elution of the Factor IX fraction components from the gel matrix with increasing concentrations of an eluting agent to sequentially provide a Factor II fraction, a Factor X fraction, and a Factor IX fraction.

5. The composition of claims 3 or 4, wherein the eluting agent is an aqueous solution of sodium chloride.

6. The composition of claims 3 or 4, wherein the components are eluted from the gel matrix by stepwise elution with increasing concentrations of NaCl in aqueous solution of from about 0.10 M to about 1 M.

7. The composition of claims 3 or 4, wherein the Factor II fraction is eluted with about 0.25 M NaCl, the Factor X fraction is eluted with about 0.45 M NaCl, and the Factor IX fraction is eluted with about 0.80 M NaCl.

8. The method of claim 2, wherein the clotting factor deficiency is a congenital deficiency.

9. The method of claim 2, wherein the clotting factor deficiency is an acquired deficiency.

10. The method of claim 2, wherein the clotting factor deficiency disease is hemophilia B.

11. An intermediate purified non-thrombogenic factor X concentrate containing factor X in therapeutic amounts up to a specific activity of about 39.7 (u/mg. protein), and containing factors II, VII, and IX in non-thrombogenic amounts of less than about 1%, 0.5%, and 15% by specific activity of factor X, respectively.

12. In a method for the treatment of a deficiency of factor X in humans of the type wherein a partially-purified therapeutic plasma protein fraction concentrated with respect to factors II, IX, and X, or with respect to factors II, VII, IX and X to provide a factor X concentrate is administered to correct the deficiency, the improvement comprising administering the non-thrombogenic concentrate of claim 11.

* * * * *